US006461593B1

(12) United States Patent
Hanioka et al.

(10) Patent No.: US 6,461,593 B1
(45) Date of Patent: Oct. 8, 2002

(54) THERAPY WITH COENZYME Q10 TO REDUCE SUBGINGIVAL MICROORGANISMS IN PATIENTS WITH PERIODONTAL DISEASE

(75) Inventors: Takashi Hanioka, Suita-Osaka (JP); Judson T. McRee, Lockhart, TX (US); Karl Folkers, Austin, TX (US)

(73) Assignee: Biomedical and Clinical Research, Austin, TX (US)

( * ) Notice: Subject to any disclaimer, the term of this patent is extended or adjusted under 35 U.S.C. 154(b) by 0 days.

(21) Appl. No.: 07/838,604

(22) Filed: Feb. 19, 1992

(51) Int. Cl.$^7$ .............................. A61K 7/16; A61K 7/28; A61K 9/20; A61K 38/43

(52) U.S. Cl. ........................ 424/49; 424/435; 424/440; 424/94.1; 514/690

(58) Field of Search ................................ 424/435, 440, 424/49–58, 94.1; 514/690

(56) References Cited

U.S. PATENT DOCUMENTS

| | | | | |
|---|---|---|---|---|
| 3,452,144 A | * | 6/1969 | Yamamura et al. | 514/690 |
| 3,499,088 A | * | 3/1970 | Shinkai et al. | 514/690 |
| 3,534,137 A | * | 10/1970 | Matsumura et al. | 514/690 |
| 3,769,170 A | * | 10/1973 | Kondo et al. | 435/133 |
| 3,832,460 A | * | 8/1974 | Kosti | 424/54 |
| 4,068,001 A | * | 1/1978 | Kanno | 514/690 |
| 4,068,003 A | * | 1/1978 | Miyat | 514/690 |
| 4,156,718 A | * | 5/1979 | Bliznakov | 424/94.1 |
| 4,491,594 A | * | 1/1985 | Ogawa et al. | 514/690 |
| 4,636,381 A | * | 1/1987 | Takana et al. | 514/690 |
| 4,654,373 A | * | 3/1987 | Bertelli | 514/690 |
| 4,684,520 A | * | 8/1987 | Bertelli | 424/94.1 |
| 4,778,798 A | * | 10/1988 | Brasey | 514/690 |
| 4,824,669 A | * | 4/1989 | Folkers et al. | 514/690 |
| 4,827,062 A | * | 5/1989 | Saeki et al. | 514/690 |
| 4,885,167 A | * | 12/1989 | Folkers et al. | 424/94.1 |
| 5,011,858 A | * | 4/1991 | Langsjoen et al. | 514/690 |
| 5,041,373 A | * | 8/1991 | Chambers | 435/7.9 |
| 5,082,650 A | * | 1/1992 | Folkers et al. | 514/690 |
| 5,223,264 A | * | 6/1993 | Wehling et al. | 424/44 |
| 5,470,882 A | * | 11/1995 | Dixon et al. | 514/596 |

FOREIGN PATENT DOCUMENTS

| | | | | |
|---|---|---|---|---|
| EP | 107941 | * | 5/1984 | 514/690 |
| GB | 2116426 | * | 9/1983 | 514/690 |
| JP | 61286314 | * | 12/1986 | 514/690 |
| JP | 1165522 | * | 6/1989 | 514/690 |
| JP | 54151932 | * | 6/1989 | 514/690 |
| JP | 54151933 | * | 6/1989 | 514/690 |
| WO | 86/04503 | * | 8/1986 | 514/690 |

OTHER PUBLICATIONS

Ye, Chun–qu et al., "New and Superior Conditions to Determine Levels of Coenzyme $Q_{10}$ in Mammalian Tissues," *Med. Chem. Res.*, 1:37–42, 1991, published in U.S.A.

Langsjoen, Peter H., et al., "Treatment of Patients with Human Immunodeficiency Virus Infection with Coenzyme $Q_{10}$," *Biomedical and Clinical Aspects of Coenzyme Q*, 6:409–415, 1991, published in U.S.A.

Iwamoto, Yoshifumi, et al., "Clinical Effect of Coenzyme $Q_{10}$ on Periodontal Disease," *Biomedical and Clinical Aspects of Coenzyme Q*, 3:109–119, 1981, published in U.S.A.

Page & Schroeder, "Current Status of the Host Response in Chronic Marginal Periodontitis," *J. Periodontal*, 52:477–491, 1984, published in U.S.A.

Loe & Silness, "Periodontal Disease in Pregnancy. I Prevalence and Severity," *Acta Odont. Scand.*, 22:533–551, 1963 published in Norway.

Silness & Loe, "Periodontal Disease in Pregnancy. II. Correlation Between Oral Hygiene and Periodontal Condition," *Acta Odont. Scand.*, 22:121–135, 1964, published in Norway.

Parker et al., "Leukocyte Immunophenotyping by Flow Cytometry in a Multisite Study: Standardization, Quality Control, and Normal Values in the Transfusion Safety Study," *Clin. Immun. Immunopathol.*, 55:187–220, 1990, published in U.S.A.

Hanioka et al., "Haemoglobin Concentration and Oxygen Saturation in Dog Gingiva with Experimentally Induced Periodontitis," *Archs. Oral. Biol.*, 34:657–663, 1989, published in Great Britain.

(List continued on next page.)

*Primary Examiner*—Shep K. Rose
(74) *Attorney, Agent, or Firm*—Arnold, White & Durke

(57) ABSTRACT

The presence of diverse microorganisms in the gingiva of patients having periodontal disease is very well known to be deleterious to gingival health, and particularly to facilitate the appearance and development of dental cavities. Such microorganisms are always associated with periodontal disease, and if such microorganisms remain unchecked or uncontrolled, extraction of teeth are likely to occur.

In the past, the presence of microorganisms in the gingiva of patients with periodontal disease has been periodically and erratically treated with anti-microbial agents, including antibiotics. For anti-microbial agents and antibiotics to be effective in the gingiva, such agents and antibiotics must come into direct contact with microorganisms, and such contact is known to be incomplete, partly because there may be barriers of fluid and tissue which prevent direct contact between the agents and antibiotics with the microorganisms. Also, such agents can be inactive for certain microorganisms and even when there is activity, such microorganisms can become metabolically resistant to the agents and antibiotics.

A more effective way to reduce and to control microorganisms in the gingiva of patients with periodontal disease is to increase the efficacy of the immune system of the host. Coenzyme $Q_{10}$ ($CoQ_{10}$) has been known to increase the immune system, but previously it was unknown that $CoQ_{10}$ could be a very effective mechanism to reduce and to eliminate microorganisms in the gingiva of patients with periodontal disease.

3 Claims, No Drawings

OTHER PUBLICATIONS

Hanioka et al., "Hemoglobin Concentration and Oxygen Saturation of Clinically Healthy and Inflamed Gingiva in Human Subjects," *J. Periodont. Res.,* 25:93–98, 1990, published in Denmark.

Kinane et al., "Depressed Helper–To–Suppressor T–Cell Rations in Early–Onset Forms of Periodontal Disease," *J. Periodont. Res.,* 24:161–164, 1989, published in Denmark.

Stashenko et al., "T Cell Responses of Periodontal Disease Patients and Healthy Subjects to Oral Microorganisms," *J. Periodont. Res.,* 18:587–600, 1983, published in Denmark.

Stashenko et al., "Helper and Suppressor T Cells in Periodontal Disease," *J. Periodontal. Res.,* 20:515–521, 1985, published in Denmark.

Jully et al., "Immunohistological Identification of Cell Subsets in Human Gingiva After Locat Treatment for Gingivitis or Periodontitis," *J. Clin. Periodont.,* 13:223–227, 1986, published in Denmark.

Keyes et al., "The Use of Phase–Contrast Microscopy and chemotherapy in the Diagnosis and Treatment of Periodontal Lesions—An Initial Report," *Quintessence Int.,* 2:69–76, 1978, published in U.S.A.

Listgarten & Hellden, "Relative Distribution of Bacteria at Clinically Healthy and Periodontally Diseased Sites in Humans," *J. Clin. Periodont.,* 5:115–132, 1978, published in Denmark.

Lindhe et al., "Some Microbiological and Histopathological Features of Periodontal Disease in Man," *J. Periodontal,* 51:264–269, 1980, published in U.S.A.

Savitt & Socransky, "Distribution of Certain Subgingival Microbial Species in Selected Periodontal Conditions" *J. Periodontal. Res.,* 19:111–123, 1984, published in Denmark.

Tanner H.A., "The Relationship of Citrates to Periodontal Disease," *J. Periodontol.,* 38:242, 1967, published in U.S.A.

Tsunemitsu et al., "Effect of Ubiquinone 35 on Hypercitricemia," *J. Periodontol.,* 39:215, 1968, published in U.S.A.

Tsunemitsu & Matsumura, "Effect of Coenzyme Q Administration on Hypercitricemia of Patients with Periodontal Disease," *J. Dent. Res.,* 46:1382, 1967, published in U.S.A.

Littarru et al., "Deficiency of Coenzyme $Q_{10}$ in Gingival Tissue from Patients with Periodontal Disease," *Proc. Natl. Acad. Sci.,* 68:2332–2335, 1971, published in U.S.A.

Wilkinson et al., "Bioenergetics in Clinical Medicine. II. Adjunctive Treatment with Coenzyme Q in Periodontal Therapy," *Res. Com. Chem. Path. Pharm.,* 12:111–124, 1975, published in U.S.A.

Wilkinson et al., "Bioenergetics in Clinical Medicine. IV. Adjunctive Treatment of Periodontal Disease with Coenzyme $Q_{10}$," *Res. Com. Chem. Path. Pharm.,* 14:715–719, 1976, published in U.S.A.

Shizukuishi et al., "Clinical Effect of Coenzyme $Q_{10}$ on Periodontal Disease; Evaluation of Oxygen Utilization in Gingiva by Tissue Reflectance Spectrophotometry," *Biomedical and Clinical Aspects of Coenzyme Q*, vol. 5, Folkers & Yamaura eds., Elsevier Science Publishers, pp. 359–368, 1986, published in New York.

Shizukuishi et al., "Effect of Coenzyme $Q_{10}$ on Experimental Periodontitis in Dogs," *Biomed. Res.,* 4:33–40, 1983, published in U.S.A.

Lenaz et al., "Organic Structural Specificity and sites of Coenzyme Q in Succinoxidase and DPNH–Oxidase Systems," *Arch. Biochem. Biophys.,* 123(3):539–550, 1968, published in U.S.A.

Wilkinson et al., "Adjunction Treatment with Coenzyme $Q_7$ of Periodontal Disease," *IRCS,* 4:428–429, 1976, published in United Kingdom.

Matsumura et al., "Evidence for Enhanced Treatment of Periodontal Disease by Therapy with Coenzyme Q," *Int. J. Vit. Nutr. Res.,* 43(4):537–548, 1973, published in Europe.

Iwamoto et al., "Study of Periodontal Disease and Coenzyme Q," *Res. Commun. Chem. Pathol. Pharmacol.,* 11(2):265–271, 1975, published in U.S.A.

Nakamura e al., "Study of $CoQ_{10}$–Enzyme in Gingiva from Patients with Periodontal Disease and Evidence for a Deficiency of Coenzyme $Q_{10}$," *Proc. Natl. Acad. Sci.,* 71(4):1456–1460, 1974, published in U.S.A.

Wilkinson et al., Presentation by Edward G. Wilkinson at the 61st Annual Meeting of the American Academy of Periodontology, Sep. 24–27 in Minneapolis, Minnesota, 1975, published in U.S.A.

Hansen et al., "Bioenergetics in Clinical Medicine. IX. Gingival and Leucocytic Deficiencies of Coenzyme $Q_{10}$ in Patients with Periodontal Disease," *Res. Comm. Chem. Path. Pharmacol.,* 14(4):729–738, 1976, published in U.S.A.

Folkers et al., "Bioenergetics in Clinical Medicine. X. Survey of the Adjunctive Use of Coenzyme Q with Oral Therapy in Treating Periodontal Disease," *J. Medicine,* 8(5):333–348, 1977, published in U.S.A.

Folkers et al., "Inhibition by Adriamycin of the Mitochondrial Biosynthesis of Coenzyme $Q_{10}$ and Implication for the Cardiotoxicity of Adriamycin in Cancer Patients," *Biochem. Biophys. Res. Comm.,* 77:1536, 1977, published in U.S.A.

Wilkinson et al., "Treatment of Periodontal and Other Soft Tissue Disease of the Oral Cavity with Coenzyme Q," *Proceedings of the International Symposium of Coenzyme Q,* Elsevier–North Holland Biomedical Press B.V., vol. 1, pp. 251–266, 1977, published in U.S.A. and the Netherlands.

Wilkinson et al., "Treatment of Peridontal and Other Soft Tissue Disease of the Oral Cavity with Coenzyme Q," Abstract from the International Symposium on Coenzyme Q—Biomedical and Clinical Aspects, Sep. 15–18, 1976 in Japan, p. 62, published in Japan.

Wilkinson & Folker, "Measuring Changes in the Health of the Periodontium and Other Oral Tissues," Abstract for the 3rd International Symposium on Coenzyme Q in Austin, Texas, Jan. 18–21, 1981, published in U.S.A.

Iwamoto et al., "Clinical Effect of Coenzyme $Q_{10}$ on Periodontal Disease," Abstract for the 3rd International Symposium on Coenzyme Q—Biomedical and Clinical Aspects, in Austin, Texas, Jan. 18–21, 1981, published in U.S.A.

Nylander & Nordlund, "Clinical Effects on Periodontal Status After Given Oral Supplement of Ubiquinone Coenzyme $Q_{10}$," *Swedish Journal of Biological Medicine,* 1(4):6–11, 1991, published in Sweden.

\* cited by examiner

THERAPY WITH COENZYME Q10 TO REDUCE SUBGINGIVAL MICROORGANISMS IN PATIENTS WITH PERIODONTAL DISEASE

BACKGROUND OF THE INVENTION

This invention relates to a new and very safe therapy which involves treatment with coenzyme $Q_{10}$ ($CoQ_{10}$) of patients in the normal practice of dentistry who have periodontal disease. The gingiva of these patients with periodontal disease are afflicted with diverse microorganisms which are the primary cause of the initiation and development of dental caries and loss of bone support.

There has never been a completely effective and safe therapy to diminish or eradicate microorganisms in periodontal disease. Anti-microbial agents and antibiotics have been used but have never been totally effective, although they have been widely and commonly used in dental practice across the country. Many periodontal patients do not respond to treatment with such agents and antibiotics.

Many or most patients with periodontal disease have depressed immune systems which allow the growth and presence of microorganisms in the diseased gingiva. A new and far better approach to reduce subgingival microorganisms of patients with periodontal disease is to rejuvenate the depleted immune system of patients.

The human immune system is very complex and incompletely understood. No therapeutic approach has heretofore been established to improve the immune system and thereby reduce microorganisms in diseased gingiva. There are at least two general approaches for stimulation of the immune system by biochemical mechanisms. One such approach is to use immune stimulants which are foreign to the human body and which may be categorized as non-specific adjuvants or medicinals. A second and far better approach is to activate intrinsic mechanisms of the immune system by using substances which are normally present in human tissue, and which are known to stimulate the immune system. This latter approach has the advantage of avoiding undesirable side effects commonly associated with non-specific medicinals foreign to the human body, but which can stimulate the immune system.

T4 helper-inducer lymphocytes facilitate plasma cells to secrete antibodies, induce maturation of T8 cytotoxic cells, and suppress maturation of B-cells. The T4 helper-inducer lymphocytes may induce maturation of B-cells, proliferation of memory clones, and induce T8 suppressor cells. In turn, the T8 suppressor cells are known to suppress differentiation to T8 cells by the participation of a suppressor factor. It is known that $CoQ_{10}$ is stimulatory of the immune system in vivo as may be monitored by the ratio of T4/T8 lymphocytes.

Bliznakov et al. used $CoQ_{10}$ to treat mice susceptible to tumors which may be induced by dibenzpyrene. Bliznakov et al. observed a resultant reduction of the percentage of mice with tumors, and a reduction in the tumor size or number of those mice that developed tumors, as well as an increase in the number of survivors (*Experientia*, 26; 953–954 (1970). Also, Bliznakov et al. investigated a parasitic model which consisted of mice that had been infected with the malarial organism, *Plasmodium berghei*. Bliznakov et al. found the $CoQ_{10}$ potentiated the effectiveness of chloroquin, increased survivors, prolonged the survival time, and reduced the parasitemia in the red blood cells of mice infected with this malarial organism. Bliznakov et al. therefore, had demonstrated that $CoQ_{10}$ interacted in the mechanisms of the immune system (*Book of Abstracts, VI International Meeting of the Reticuloendothelial Society*, Freiburg, Germany, p. 14 (1970); Bliznakov et al., The Reticuloendothelial System and Immune Phenomena, edited by DiLuzio, N. R., Plenum Press, N.Y., 315–322 (1971).

A technique for controlling and/or reversing immunological senescence in animals was found by administering $CoQ_{10}$ (U.S. Pat. No. 5,011,858).

The present invention resulted from experimentation directed toward minimizing and even eliminating microorganisms present in the diseased gingiva of patients having periodontal disease.

SUMMARY OF THE INVENTION

Twenty-two patients with periodontal disease, 11 males and females, ages 22 to 66, were orally treated with 100 mg of $CoQ_{10}$ for two months. The gingival index decreased ($p<0.01$), the pocket depth decreased ($p<0.001$), but the plaque index did not change. Of the subgingival microorganisms, motile rods decreased ($p<0.01$) and spirochetes decreased ($p<0.02$). In 4/22 patients, all motile microorganisms in the gingiva remarkably disappeared. The T4/T8 ratios increased ($p<0.001$); the blood levels of $CoQ_{10}$ increased ($p<0.001$).

For convenience of patients, this therapeutic trial with $CoQ_{10}$ was limited to only two months. $CoQ_{10}$ is not a drug, but is intrinsic to the bioenergetics of the immune system and to the gingival metabolism. Therapy with $CoQ_{10}$ at a higher dose level and/or beyond two months is even more therapeutically effective.

DESCRIPTION OF THE PREFERRED EMBODIMENT

A deficiency of coenzyme $Q_{10}$ was found in human inflamed gingiva (1), and was a basis for therapy to increase the level of $CoQ_{10}$ in the diseased tissue. Then, several clinical trials with administration of $CoQ_{10}$ to patients with periodontal disease were conducted. These trials demonstrated an improvement of the periodontal pocket depth (2–5), gingival inflammation (2,3,5) and tooth mobility (3–5).

Recently, Langsjoen et al. demonstrated that $CoQ_{10}$ enhanced the host defense mechanisms in patients with AIDS and the AIDS-related complex. It has been known that bacterial plaque is the primary etiologic factor and that systemic disorders enhance periodontitis. However, there is considerable individual variation in the host response to the microbial challenge (7). Imbalance in host/parasite relationships may be precipitated by either alterations in the periodontal microbial flora or host responses to the microorganisms. The present invention relates to a clinical trial comparing subgingival microbial flora before and during the administration of $CoQ_{10}$ to patients with periodontal disease.

Materials Methods and Examples

Twenty-two systemically healthy patients with periodontal disease, 11 males and 11 females, ages 33 to 66, participated in this trial. These volunteers were treated orally with 100 mg of $CoQ_{10}$ per day for two months. Informed consent forms were signed prior to the study. Periodontal examinations and peripheral blood analyses were made before and during the trial. During the trial, the patients were not provided any routine periodontal treatment, and the staff gave them no information about oral hygiene to the patients.

The gingival index (8) and plaque index (9) were criteria to assess to degrees of gingival inflammation and accumulation of plaque on the teeth, respectively. The periodontal pocket depth was measured in interdental regions of buccal gingiva. The deepest pocket which was measured before administration of $CoQ_{10}$ was selected for direct examination of oral bacteria by a microscope. The subgingival plaques were obtained with a curette, and were then dispersed in physiological saline which contained 1% gelatin, and were then prepared for analysis by phase contrast microscopy and were then prepared for analysis by phase contrast microscopy. The biopsies were viewed by means of a DS/300 microscope system (Dental Scientific Systems, Inc., VA) at 400× magnification. Small spirochetes, large spirochetes, spinning rods, spiral rods, small gliding rods, large gliding rods and palisading rods were identified as based upon cellular morphology and active motility. The following scores were used in each category: 0, no bacterial cells; 1, 1–9 cells; 2, 10–39 cells; and 3, more than 40 cells.

About 3 ml of peripheral blood was drawn for determination of $CoQ_{10}$ levels and the T4/T8 ratios. The determination of the $COQ_{10}$ level was performed as described by Ye et al. (10). T4(CD4) and T8 (CD8) monoclonal antibodies were purchased from Coulter Immunology, Hialeah, Fla. The lymphocytes were stained according to the two-color fluorescence, and the flow cytometric analysis was performed on an Epics Profile cell sorter (Coulter Electronics Inc., Hileah, Fla.). The sample preparations and staining procedures were performed as described by Parker et al. (11).

A paired-t test was used for the statistical analysis of differences in the gingival index, the plaque index, the blood $CoQ_{10}$ levels, and the T4/TS ratios before and after the administration. The Wilcoxson test was used to test scores in microscopic analysis.

Results Constituting the Discovery

The changes in the gingival index, plaque index and pocket depth following the administration of $CoQ_{10}$ are shown in Table 1.

TABLE 1

Changes of Gingival Index, Plaque Index and Pocket Depth Before and After Administration of $CoQ_{10}$ for 2 Months

| ID # | Sex | Age | Gingival Index | | Plaque Index | | Pocket Depth (mm) | |
|---|---|---|---|---|---|---|---|---|
| | | | Before | 2 Months | Before | 2 Months | Before | 2 Months |
| 1 | F | 44 | 1.2 | 0.8 | 0.1 | 0.1 | 2.8 | 2.8 |
| 2 | F | 46 | 0.7 | 0.5 | 0.0 | 0.0 | 2.8 | 2.3 |
| 3 | M | 48 | 1.5 | 0.7 | 0.3 | 0.6 | 3.0 | 2.7 |
| 4 | M | 39 | 1.5 | 0.5 | 0.3 | 0.3 | 2.8 | 2.7 |
| 5 | F | 66 | 0.3 | 0.1 | 0.1 | 0.2 | 2.2 | 1.9 |
| 6 | F | 56 | 0.4 | 0.2 | 0.0 | 0.0 | 2.5 | 2.4 |
| 7 | M | 46 | 0.8 | 0.5 | 0.2 | 0.2 | 3.1 | 2.6 |
| 8 | F | 38 | 0.5 | 0.2 | 0.1 | 0.1 | 3.3 | 2.9 |
| 9 | F | 43 | 0.2 | 0.1 | 0.2 | 0.2 | 3.8 | 2.9 |
| 10 | M | 61 | 0.5 | 0.3 | 0.5 | 0.6 | 2.4 | 2.2 |
| 11 | M | 33 | 0.9 | 0.7 | 0.3 | 0.4 | 2.4 | 2.3 |
| 12 | M | 53 | 1.0 | 1.0 | 2.0 | 2.0 | 2.2 | 1.8 |
| 13 | M | 53 | 1.2 | 1.0 | 0.0 | 0.0 | 4.4 | 3.6 |
| 14 | F | 66 | 0.3 | 0.3 | 0.0 | 0.0 | 3.5 | 3.4 |
| 15 | F | 34 | 1.9 | 1.4 | 0.3 | 0.4 | 2.4 | 2.8 |
| 16 | M | 36 | 0.3 | 0.2 | 0.0 | 0.0 | 3.0 | 2.6 |
| 17 | M | 64 | 0.6 | 0.3 | 0.1 | 0.2 | 2.5 | 2.3 |
| 18 | F | 43 | 0.6 | 0.7 | 0.2 | 0.1 | 2.9 | 2.5 |
| 19 | F | 61 | 2.0 | 1.4 | 0.4 | 0.4 | 3.5 | 3.0 |
| 20 | F | 57 | 1.6 | 1.1 | 0.7 | 0.6 | 4.7 | 4.5 |
| 21 | M | 47 | 1.8 | 1.3 | 0.4 | 0.3 | 4.1 | 3.7 |
| 22 | M | 46 | 0.6 | 0.4 | 0.1 | 0.1 | 2.7 | 2.6 |

TABLE 1-continued

Changes of Gingival Index, Plaque Index and Pocket Depth Before and After Administration of $CoQ_{10}$ for 2 Months

| ID # | Sex | Age | Gingival Index | | Plaque Index | | Pocket Depth (mm) | |
|---|---|---|---|---|---|---|---|---|
| | | | Before | 2 Months | Before | 2 Months | Before | 2 Months |
| Mean + S.D. | | | 0.9 + 0.6 | 0.6 + 0.4 | 0.3 + 0.4 | 0.3 + 0.4 | 3.0 + 0.7 | 2.8 + 0.6 |
| t value | | | 5.437 | | 1.226 | | 5.037 | |
| p value | | | <0.001 | | N.S.* | | <0.001 | |

*not significant

The gingival index and pocket depth decreased, and the decreases are highly significant. The plaque index showed no change.

Table 2 shows that the changes of scores in microscopic analyses in subgingival microorganisms after taking $COQ_{10}$.

TABLE 2

Changes of Subgingival Microorganism Before and After Administration of $CoQ_{10}$ for 2 Months Analyzed Using Phase Contrast Microscopy

| ID # | Motile Rods* | | Spirochetes** | | Total | |
|---|---|---|---|---|---|---|
| | Before | 2 Months | Before | 2 Months | Before | 2 Months |
| 1 | 0# | 0 | 3 | 0 | 3 | 0 |
| 2 | 2 | 1 | 1 | 0 | 3 | 1 |
| 3 | 1 | 0 | 1 | 0 | 2 | 0 |
| 4 | 1 | 3 | 3 | 3 | 4 | 6 |
| 5 | 3 | 3 | 1 | 0 | 4 | 3 |
| 6 | 3 | 0 | 0 | 0 | 3 | 0 |
| 7 | 6 | 4 | 6 | 4 | 12 | 8 |
| 8 | 0 | 0 | 2 | 1 | 2 | 1 |
| 9 | 1 | 1 | 1 | 1 | 2 | 2 |
| 10 | 3 | 2 | 4 | 3 | 7 | 5 |
| 11 | 2 | 2 | 6 | 6 | 8 | 8 |
| 12 | 5 | 2 | 3 | 1 | 8 | 3 |
| 13 | 0 | 0 | 6 | 6 | 6 | 6 |
| 14 | 6 | 6 | 2 | 0 | 8 | 6 |
| 15 | 5 | 3 | 3 | 3 | 8 | 6 |
| 16 | 3 | 0 | 3 | 0 | 6 | 0 |
| 17 | 4 | 4 | 3 | 3 | 7 | 7 |
| 18 | 6 | 3 | 3 | 3 | 9 | 6 |
| 19 | 2 | 0 | 3 | 3 | 5 | 3 |
| 20 | 6 | 5 | 1 | 3 | 7 | 8 |
| 21 | 6 | 3 | 3 | 3 | 9 | 6 |
| 22 | 2 | 1 | 3 | 2 | 5 | 3 |
| p value## | <0.01 | | <0.02 | | <0.01 | |

*Sum of scores in small and large spirochtes.
**Sum of scores in spinning, spiral, small gliding, large gliding and palisading motile rods.
Following scores were used in each category: 0, no motile cells; 1, 1–9 cells; 2, 10–39 cells; 3, more than 40 cells were detected in a microscopic field.
**analyzed by the Wilcoxen test.

The scores in the categories are summarized into either motile rods or spirochetes. Both types of motile microorganism show significant reduction after the administration. In four patients, the microorganisms remarkably disappeared.

Table 3 shows the results from peripheral blood analyses.

TABLE 3

Changes of T4/T8 Ratio and Blood $CoQ_{10}$ Level Before and After Administration of $CoQ_{10}$ for 2 Months

| ID # | T4/T8 Ratio Before | T4/T8 Ratio 2 months | $CoQ_{10}$ level (ug/ml) Before | $CoQ_{10}$ level (ug/ml) 2 months |
|---|---|---|---|---|
| 1 | 1.8 | 2.4 | 1.00 | 1.57 |
| 2 | 3.8 | 3.6 | 0.71 | 1.26 |
| 3 | 3.9 | 3.8 | 0.70 | 1.17 |
| 4 | 2.4 | 2.3 | 0.61 | 1.60 |
| 5 | 2.1 | 3.1 | 0.81 | 1.94 |
| 6 | 2.5 | 2.8 | 0.75 | 1.59 |
| 7 | 3.6 | 4.9 | 0.80 | 2.29 |
| 8 | 2.4 | 2.8 | 0.71 | 2.39 |
| 9 | 3.4 | 3.5 | 0.62 | 1.16 |
| 10 | 3.6 | 4.0 | 1.00 | 1.99 |
| 11 | 1.7 | 1.9 | 0.64 | 1.44 |
| 12 | 2.4 | 2.7 | 1.14 | 2.37 |
| 13 | 5.5 | 7.1 | 0.92 | 1.72 |
| 14 | 2.1 | 3.7 | 0.76 | 2.22 |
| 15 | 2.2 | 2.0 | 0.57 | 1.30 |
| 16 | 4.9 | 6.2 | 0.79 | 2.10 |
| 17 | 2.3 | 2.9 | 1.20 | 1.88 |
| 18 | 1.9 | 2.0 | 0.81 | 1.65 |
| 19 | 2.2 | 3.2 | 0.89 | 1.75 |
| 20 | 3.3 | 3.2 | 0.91 | 1.74 |
| 21 | 2.7 | 3.9 | 1.18 | 1.90 |
| 22 | 2.8 | 3.4 | 0.61 | 1.55 |
| Mean + S.D. | 2.9 + 1.0 | 3.4 + 1.3 | 0.82 + 0.19 | 1.75 + 0.37 |
| t value | 4.317 | | 13.209 | |
| p value | <0.001 | | <0.001 | |

The T4/T8 ratio significantly increased, and the increase is evident in 17 patients out of 22. The blood $CoQ_{10}$ levels increased in all of the patients.

Significance of the Discovery

Recently, Hanioka et al. suggested that the needed oxygen supply to inflamed gingiva may be increased to some extent, but not sufficiently to fulfill the requirement for the needed oxygen in dogs (12) and in humans (13). The oral administration of $COQ_{10}$ was shown to increase $COQ_{10}$ levels and activities of the $CoQ_{10}$-dependent enzymes in inflamed dog gingiva (14), and oxygen utilization in inflamed human gingiva (5). Thus, the decreases in gingival index and pocket depth seem to result from correction of a deficiency of $CoQ_{10}$ and the restoration of the metabolic energy required for the diseased tissue. The decreases in pocket depth were positive, but the gingival inflammation did not recover during the limited 2-month trial. Accordingly, administration of $COQ_{10}$ to patients with periodontal disease will prove even more beneficial when continued longer than 2 months, and also may be considered as adjunctive treatment with current dental practice, as suggested by Wilkinson et al. (2,3).

T4 lymphocytes are known to regulate the immune response, and the T4/T8 ratios have been widely used as a parameter for the evaluation of immunologic disorders. Several studies on T4/T8 ratios from patients with periodontal disease have been reported, as follows. Kinane et al. (15) found depressed T4/T8 ratios in early onset forms of periodontal disease. Stashenko et al. (16, 17) demonstrated that patients with low T4/TS ratios had lower T cell response levels to oral microorganisms, and more redness and bleeding on probing than did those with higher T4/T8 ratios. Reduced T4/T8 ratios were demonstrated in diseased human periodontal tissues which indicated a role for T-cells in periodontitis (18). Our demonstrating an increase in T4/T8 ratios from the oral administration of $CoQ_{10}$ is apparently beneficial to improve the diseased tissue.

Others have had an interest in the motility as observed in subgingival plaque biopsies by microscopic study as a measure of disease or as a predictor of future periodontal disease (19). It has been known that data from phase contrast and dark field microscopic analyses have correlated with clinical features of periodontal disease, and that the ratio of motile rods and spirochetes increased during disease of periodontal tissue (20–22). These prior investigations indicated that increased motility can be useful as a criterion of increased microbial disease. Oral administration of $CoQ_{10}$ decreases motility and improves periodontal health.

It is more evident that periodontal disease is correlated with actual tissue destruction which is caused by an imbalance in host defense/parasite equilibrium. Environmental factors, such as plaque accumulation, can shift the host defense/parasite balance in favor of the microflora. Our trial was planned so that the environmental factor of plaque would not change. No significant change was observed in plaque accumulation for our patients.

Therefore, it has been shown that the administration of $CoQ_{10}$ does improve the host defense mechanism, and causes an improved host defense/parasite equilibrium, as demonstrated by increased T4/T8 ratios and by reduced numbers or motile microorganisms. Transient fluctuations in the most defense/parasite equilibrium may result in cycles of either diminished or increased intensity of the inflammatory disease. Therapy with $CoQ_{10}$ reduces periodontal disease and prolongs periods of natural remission which occurs during periods of active disease.

Therapeutic Routes of Administration of $CoQ_{10}$

The discovery of the utility of coenzyme $Q_{10}$ ($CoQ_{10}$) to reduce and even eliminate microorganisms in diseased gingival tissue was based upon the oral administration of capsules containing $CoQ_{10}$ dissolved in soybean oil. This oral route of administration of $CoQ_{10}$ differentiated the enhancement of the immune system to reduce the microorganisms in contrast to the topical use of anti-microbulations and antibiotics in ordinary dental practice.

Normal, healthy gingival tissue contains $CoQ_{10}$ on a natural and intrinsic basis. It is understood that diseased gingival tissue with microorganisms has a deficiency of $CoQ_{10}$, and that correction of the deficiency improves the mechanisms of the immune system in the gingival tissue. Therefore, topical treatment of diseased gingival tissue with microorganisms with toothpastes containing $CoQ_{10}$ is another route of administration. In addition to the use of toothpastes containing $CoQ_{10}$, diverse mouthwashes containing $CoQ_{10}$ are applicable.

The use of tooth pastes and mouthwashes containing $CoQ_{10}$ allow contact of gingival tissue with formulations containing $CoQ_{10}$ for only the minutes that the patients utilize the toothpastes or mouthwashes containing $CoQ_{10}$.

Oral formulations containing $CoQ_{10}$ in lozenges that slowly dissolve in the mouth over prolonged periods of time, beyond a few minutes, are particularly therapeutically effective to reduce the microorganisms in diseased gingival tissue. Not only are $CoQ_{10}$-lozenges topically effective, but that portion of the $CoQ_{10}$ in the lozenges which is not absorbed by the gingival tissue, but is swallowed, is effective orally.

The references cited in this application are incorporated by reference in pertinent part herein for the reasons cited.

References

1. Littarru et al., *Proc. Natl. Acad. Sci.*, 68:2332–2335 (1971).
2. Wilkinson, et al., *Res. Com. Chem. Path. Pharm.*, 12:111–124 (1975).

3. Wilkinson et al., *Res. Com. Chem. Path. Pharm.,* 14:715–719 (1976).
4. Iwamoto et al., "Clinical Effect of Coenzyme $Q_{10}$ on Periodontal Disease" Biomedical and Clinical Aspects of Coenzyne Q, Vol. 3, Folkers, K. and Yamamura Y. eds., Elsevier Science Publishers, New York, pp. 109–119 (1981).
5. Shizukuishi et al., "Evaluation of Oxygen Utilization in Gingiva by Tissue Reflectance Spectrophotometry", Biomedical and Clinical Aspects of Coenzyme Q, Vol. 5, Folkers, K. and Yamamura, Y. eds., Elsevier Science Publishers, New York, pp. 359–368 (1986).
6. Langsjoen et al., "Treatment of Patients with Human Immunodeficiency Virus Infection with Coenzyme $Q_{10}$", Biomedical and Clinical Aspects of Coenzyme Q, Vol. 6, Folkers, K., Littarru, G. P. and Yamagami, T., eds., Elsevier Science Publishers, New York, pp. 409–416 (1991).
7. Page et al., *J. Periodontal.,* 52:477–491 (1981).
8. Loe et al., *Acta Odont. Scand.,* 22:533–551 (1963).
9. Silness et al., *Acta Odont. Scand.,* 22:121–135 (1964).
10. Ye et al., *Med. Chem. Res.,* 1:37–42 (1991).
11. Parker et al., *Clin. Immun. Immunopathol.,* 55:187–220 (1990).
12. Hanioka et al., *Archs. Oral. Biol.,* 34:657–663 (1989).
13. Hanioka et al., *J. Periodont. Res.,* 25:93–98 (1989).
14. Shizukuishi et al., *Biomed. Res.,* 4:33–40 (1983).
15. Kinane et al., *J. Periodont. Res.,* 24:161–164 (1988).
16. Stashenko et al., *J. Periodont. Res.,* 18:587–600 (1983).
17. Stashenko et al., *J. Periodont. Res.,* 20:515–521 (1985).
18. Jully et al., *J. Clin. Periodont.,* 13:223–227 (1986).
19. Keyes et al., *Quintessence Int.,* 9:69–76 (1978).
20. Listgarten et al., *J. Clin. Periodont.,* 5:115–132 (1978).
21. Lindhe et al., *J. Periodontal,* 51:264–269 (1980).
22. Savitt et al., *J. Periodont. Res.,* 19:111–123 (1984).

What is claimed is:

1. A method to reduce or eliminate motile microorganisms in diseased gingival tissue of patients with periodontal disease, the method comprising contacting said motile microorganisms with a therapeutically effective amount of coenzyme $Q_{10}$.

2. The method of claim 1 wherein the contacting of motile microorganisms comprises contact with lozenges containing coenzyme $Q_{10}$ which dissolve in the mouth over prolonged periods of time and expose motile subgingival microbial flora, spirochetes, motile rods and other motile microorganisms present in diseased gingival tissue to contact with coenzyme $Q_{10}$.

3. A method to inhibit microbial growth in gingival tissue comprising exposing motile subgingival microbial flora, spirochetes, motile rods and other motile microorganisms present in said tissue to a therapeutically effective amount of coenzyme $Q_{10}$.

* * * * *